United States Patent
Reeve et al.

(10) Patent No.: US 9,655,939 B2
(45) Date of Patent: May 23, 2017

(54) ANTIMICROBIAL AND/OR ANTIVIRAL COMPOSITION AND TO METHODS FOR PREPARING AND ADMINISTERING SAME

(75) Inventors: Robert Alan Reeve, Hillsburgh (CA); Theodore Philip James Michael, Hillsburgh (CA)

(73) Assignee: Robert Alan Reeve, Ontario (CA)

( * ) Notice: Subject to any disclaimer, the term of this patent is extended or adjusted under 35 U.S.C. 154(b) by 750 days.

(21) Appl. No.: 11/572,849

(22) PCT Filed: Jul. 29, 2005

(86) PCT No.: PCT/CA2005/001187
§ 371 (c)(1),
(2), (4) Date: Nov. 19, 2007

(87) PCT Pub. No.: WO2006/010269
PCT Pub. Date: Feb. 2, 2006

(65) Prior Publication Data
US 2008/0063735 A1 Mar. 13, 2008

Related U.S. Application Data

(60) Provisional application No. 60/591,864, filed on Jul. 29, 2004.

(51) Int. Cl.
| | | |
|---|---|---|
| A61K 36/53 | (2006.01) |
| A01N 65/00 | (2009.01) |
| A61K 8/34 | (2006.01) |
| A61K 8/92 | (2006.01) |
| A61K 31/155 | (2006.01) |
| A61K 36/15 | (2006.01) |
| A61K 36/185 | (2006.01) |
| A61K 36/28 | (2006.01) |
| A61K 36/738 | (2006.01) |
| A61K 36/752 | (2006.01) |
| A61K 36/898 | (2006.01) |
| A61K 36/899 | (2006.01) |
| A61Q 17/00 | (2006.01) |
| A01N 65/06 | (2009.01) |
| A01N 65/08 | (2009.01) |
| A01N 65/12 | (2009.01) |
| A01N 65/22 | (2009.01) |
| A01N 65/34 | (2009.01) |
| A01N 65/36 | (2009.01) |
| A01N 65/40 | (2009.01) |
| A01N 65/42 | (2009.01) |
| A61K 9/107 | (2006.01) |

(52) U.S. Cl.
CPC .............. *A61K 36/53* (2013.01); *A01N 65/00* (2013.01); *A01N 65/06* (2013.01); *A01N 65/08* (2013.01); *A01N 65/12* (2013.01); *A01N 65/22* (2013.01); *A01N 65/34* (2013.01); *A01N 65/36* (2013.01); *A01N 65/40* (2013.01); *A01N 65/42* (2013.01); *A61K 8/34* (2013.01); *A61K 8/922* (2013.01); *A61K 31/155* (2013.01); *A61K 36/15* (2013.01); *A61K 36/185* (2013.01); *A61K 36/28* (2013.01); *A61K 36/738* (2013.01); *A61K 36/752* (2013.01); *A61K 36/898* (2013.01); *A61K 36/899* (2013.01); *A61Q 17/005* (2013.01); *A61K 9/107* (2013.01)

(58) Field of Classification Search
None
See application file for complete search history.

(56) References Cited

U.S. PATENT DOCUMENTS

| | | | |
|---|---|---|---|
| 5,403,587 A | 4/1995 | McCue et al. | |
| 5,980,925 A * | 11/1999 | Jampani et al. | 424/405 |
| 6,022,551 A * | 2/2000 | Jampani et al. | 424/405 |
| 6,114,298 A | 9/2000 | Petri et al. | |
| 6,248,343 B1 | 6/2001 | Jampani et al. | |
| 6,346,281 B1 | 2/2002 | DeAth et al. | |
| 6,488,942 B1 | 12/2002 | Ingemann | |
| 6,537,955 B1 * | 3/2003 | Raso et al. | 510/218 |
| 6,846,498 B2 | 1/2005 | DeAth et al. | |
| 6,884,763 B2 | 4/2005 | Willard et al. | |
| 2003/0064120 A1 | 4/2003 | Librizzi et al. | |

FOREIGN PATENT DOCUMENTS

| | | |
|---|---|---|
| AU | 200049078 | 11/2001 |
| CA | 2406558 | 11/2001 |
| DE | 198 07 433 A1 | 8/1999 |

(Continued)

OTHER PUBLICATIONS

Jacobelli-Turi et al., Ind. Eng. Chem. Process Des. Dev., Ion Extraction by Foam. Separation of Uranium from Vanadium in Carbonate Medium, 1967, 6 (2), pp. 161-162.*

(Continued)

*Primary Examiner* — Terry A McKelvey
*Assistant Examiner* — Catheryne Chen
(74) *Attorney, Agent, or Firm* — Additon, Higgins & Pendleton, P.A.

(57) ABSTRACT

The present invention provides for an antimicrobial and/or antiviral composition suitable for administration to a surface. The antimicrobial and/or antiviral composition is suitable for administration to a surface, comprising an essential oil portion; and an effective amount of a volatile liquid carrier such that a majority of the composition readily evaporates after dispersal onto the surface. The composition is compatible with and suitable for topical use with human skin. Methods of preparing and administering the antimicrobial and/or antiviral compositions are also disclosed.

26 Claims, No Drawings

(56) References Cited

FOREIGN PATENT DOCUMENTS

| EP | 0 264 660 A2 | 4/1988 |
|---|---|---|
| EP | 1278420 | 12/2005 |
| WO | WO93/07901 A1 | 4/1993 |
| WO | WO01/84936 | 11/2001 |
| WO | 2004/018003 A1 | 3/2004 |
| WO | 2005/009352 A2 | 2/2005 |

OTHER PUBLICATIONS 2004, http://www.hibiclens.com/pdfs/Hibistat-MSDS.doc.*
Minami, M. et al, "The inhibitory effect of essential oils on herpes simplex virus type 1 replication in vitro," Microbiol. Immunol., Sep. 22, 2003, vol. 47, No. 9, pp. 681-684.
Drugs Directorate Monograph, "Contact Lens Disinfectants," Health Canada, Nov. 15, 1996, entire document, especially section III a.
Hammer, et al, "Antimicrobial activity of essential oils and other plant extracts," Journal of Applied Microbiology, Feb. 2, 1999, vol. 86, pp. 985-999.
Sopwith, et al, "Preventing infection from reusable medical equipment: a systematic review," BMC Infectious Diseases, Mar. 27, 2002, vol. 2, pp. 4-14.
Foreign counterpart Application No. EP 05 77 0400 Supplementary European Search Report mailed Mar. 2, 2012.
"Guide to General Skin Cleansing at Home", http://www.hibiclens.com/retail/for/home-care, Copyrighted 2013, 1 page, downloaded from website Jan. 30, 2015.

\* cited by examiner

ANTIMICROBIAL AND/OR ANTIVIRAL COMPOSITION AND TO METHODS FOR PREPARING AND ADMINISTERING SAME

FIELD OF THE INVENTION

The present invention relates to an antimicrobial and/or antiviral composition, and to methods for preparing and administering same.

BACKGROUND OF THE INVENTION

A large percentage of the population suffers from stress, anxiety, and/or depression. Pharmaceuticals are constantly being developed in an attempt to manage or treat these illnesses. However, many pharmaceuticals also tend to have negative side effects. Accordingly, it is desirable to manage or treat these illnesses with natural products that have minimal side effects, if any.

Essential oils are natural products that can be extracted from various parts of a plant. One type of essential oil having a relatively high concentration of active ingredients is extracted from the roots of plant. Another type of essential oil having a relatively dilute concentration of active ingredients is extracted from the stems, flowers and/or fruits of a plant.

Aromatherapy involves the use of volatile essential oils to provide therapeutic benefits to humans. Aromatherapy products can be supplied in a form in which the essential oils can be melted or burned to release vapors for inhalation by a human (e.g., candles, incense, lamps, diffusers, and the like). Alternatively, aromatherapy products can be supplied in a form in which the essential oils can be topically applied so as to be additionally absorbed through the pores of the skin of a human (e.g., massage oils, bath oils, and the like).

In addition, many contagious diseases and/or pathogenic microorganisms are transmitted through touch, be it through direct human contact or through contacting unsanitized surfaces. Accordingly, it is desirable to inhibit these transmissions with natural products.

There appears to be a need for a composition that is natural and imparts antimicrobial and/or antiviral properties to applied surfaces. There also appears to be a need for a composition that not only imparts antimicrobial and/or antiviral properties but may also impart therapeutic aromatherapy properties.

SUMMARY OF THE INVENTION

The summary below is intended to introduce the reader to the invention that may consist of a combination or subcombination of some or all of the elements or steps described below or in other parts of this document.

In one aspect of the present invention, there is provided an antimicrobial and/or antiviral composition suitable for administration to a surface, comprising:

an essential oil portion; and an effective amount of a volatile liquid carrier such that a majority of the composition readily evaporates after dispersal onto the surface.

In another aspect of the present invention, there is provided a method for inhibiting growth of microorganisms and/or growth and reproduction of viruses, comprising administering to a surface the antimicrobial and/or antiviral composition of the present invention.

In yet another aspect of the present invention, there is provided use of the antimicrobial and/or antiviral composition for inhibiting growth of microorganisms and/or growth and reproduction of viruses. In another aspect of the present invention, there is provided use of the antimicrobial and/or antiviral composition in a medicament for inhibiting the growth of microorganisms and/or growth and reproduction of viruses.

In another aspect of the present invention, there is provided a method for preparing an antimicrobial and/or antiviral composition suitable for use on a surface, comprising combining an essential oil portion and an effective amount of a volatile liquid carrier such that a majority of the composition readily evaporates after dispersal onto the surface.

In another aspect of the present invention, the antimicrobial and/or antiviral composition comprises an effective amount of an essential oil portion to enhance the mood of a human.

The features and advantages of the composition of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

The present invention encompasses an antimicrobial and/or antiviral composition suitable for administration to a surface, comprising an essential oil portion and an effective amount of a volatile liquid carrier such that a majority of the composition readily evaporates after dispersal onto the surface. As a result of the administration of the antimicrobial and/or antiviral composition to the surface, harmful microorganisms and/or viruses can be significantly reduced or eliminated. This helps to prevent the spread of contagious illnesses. The composition made in accordance with the present invention is especially useful for surfaces that are known to host harmful microorganisms and/or viruses.

The antimicrobial and/or antiviral composition itself can also act as a barrier against harmful microorganisms and/or viruses. The composition is capable of providing protection, after application, up to at least about 4 hours.

The term "antimicrobial" used herein is meant to include destroying and/or inhibiting the growth of microorganisms, which encompasses any antimicrobial property such as, and without being limited thereto, disinfecting properties, sanitizing properties, and/or antiseptic properties. The antimicrobial composition described herein is capable of destroying and/or inhibiting the growth of a variety of microorganisms on surfaces including bacteria, spores and protozoan parasites.

The term "antiviral" used herein is meant to include destroying and/or inhibiting the growth and reproduction of viruses. The antiviral composition described herein is capable of destroying and/or inhibiting the growth and reproduction of a variety of viruses on surfaces including, and without being limited thereto, polio, HIV, Hepatitis A, B and C, the Norwalk virus, and others.

The antimicrobial and/or antiviral composition may impart therapeutic effects, such as, and without being limited thereto, enhancing the mood of a human. For example, the composition comprises an effective amount of an essential oil portion to enhance the mood of a human. By "enhancing the mood of a human", it is meant herein to include any type of improvement to the psychological well being of a human. Examples include, but are not limited to, the following desired psychological responses: increase in relaxation, increase in calmness, reduction in stress, reduction in anxiety, reduction in tension, alleviation of depression, increase in the level of happiness, management or reduction of pain, and management or reduction of headaches and migraines.

Suitable essential oils that can be used in the antimicrobial and/or antiviral composition are those essential oils that can be selected from unscented, scented, and combinations thereof and are compatible with and suitable for topical use with human skin. Such essential oils have a relatively dilute concentration of 'active ingredients' and may be extracted from the stems, flowers, and/or fruits of a plant. Examples of suitable essential oils include, but are not limited to, lemon oil, orange oil, lavender oil, grapefruit oil, chamomile oil, rose oil, tuberose oil, sandalwood oil, cedarwood oil, bergamot oil, benzoin resin, vanilla oil, jasmine oil, Lilly of the Valley oil, rice bran oil and mixtures thereof. Scented essential oils exhibit the ability to act therapeutically and enhance the mood of a human. Typical scented essential oils used include, but are not limited thereto, lemon oil, orange oil, lavender oil, and mixtures thereof. Non-scented essential oil(s) include, but are not limited thereto, rice bran oil.

In one aspect of the invention, the essential oil portion of the composition is present in an amount of from about 1 to about 20% by volume based on the total volume of the composition, more typically in an amount of from about 5 to about 15% by volume, and most typically in an amount of from about 6 to about 12% by volume. If unscented essential oils are used, a higher range can be used, for example, from about 1 to about 50% by volume, typically, from about 12 to about 30% by volume, more typically, from about 12 to about 18% by volume.

As appreciated by a person skilled in the art, the essential oil portion imparts the composition with moisturizing properties for increasing the emolliency of human skin when it is applied thereto. As a result, the composition has the additional benefit of alleviating dry and chapped human skin.

A suitable volatile liquid carrier has a relatively high vapor pressure such that allows it to readily evaporate after dispersal onto the surface. The volatile liquid carrier is compatible with and suitable for topical use on human skin. An effective amount of the volatile liquid carrier is included in the composition such that a majority of the composition readily evaporates after dispersal onto a surface.

In a typical embodiment of the invention, the volatile liquid carrier can comprise an alcohol. The alcohol can be selected from the group consisting of alcohols containing between 1 to 4 carbon atoms, and mixtures thereof. The typical alcohols include ethanol, such as 95% ethanol, isopropanol, and mixtures thereof. The composition can also comprise water. If water is present, the effective amount of volatile liquid carrier in the composition is greater than the amount of water in the composition such that the majority (e.g. greater than 50%) of the composition readily evaporates after dispersal onto the surface. The volatile liquid carrier may be present in an amount from about 50 to about 80% by volume based on the total volume of the antimicrobial and/or antiviral composition, more typically in an amount from about 60 to about 75% by volume, and most typically in an amount from about 60 to about 70% by volume. Various ratios of individual volatile liquids can be used.

As appreciated by a person skilled in the art, when the volatile liquid carrier is an alcohol, the alcohol also imparts additional antimicrobial properties for sanitizing and sterilizing the surfaces onto which it is applied.

One or more additional components may optionally be included in minor amounts to the composition of the present invention in order to provide additional benefits thereto. Examples of optional components include, but are not limited to, the following: (a) other antimicrobial agents may be added to further enhance the disinfectant properties of the composition (e.g., alkyltriethanolammonium chloride can be added, typically up to about 0.03% by volume based on the total volume of the antimicrobial and/or antiviral composition, benzalkonium chloride can be added, typically up to about 0.01% by volume based on the total volume of the antimicrobial and/or antiviral composition, hydrogen peroxide can be added, typically up to about 3% by volume based on the total volume of the antimicrobial and/or antiviral composition); (b) other antimicrobial agents such as antiseptics can also be added to prevent infection of a wound site on human skin by reducing or eliminating the growth of microorganisms (e.g., chlorohexidine gluconate can be added, for example, up to about 1% by volume based on the total volume of the antimicrobial composition, commonly about 0.002 ml to about 2 ml of a 4% by volume chlorohexidine gluconate solution may be part of an 8 ml sample of the antimicrobial composition, iodine can be added, typically up to about 3% by volume based on the total volume of the antimicrobial and/or antiviral composition); (c) antiviral agents; (d) anesthetics can be added to temporarily numb the pain of the portion of the skin to which the composition is applied (e.g., an effective amount of benzocaine can be added to the antimicrobial and/or antiviral composition); (e) surfactants can be added to aid in dispersion of the essential oil portion in the volatile liquid carrier; and (f) coloring agents can be added to improve the aesthetic properties of the composition. It is appreciated that only optional components that are compatible with and suitable for topical use on human skin should be added to the composition.

One embodiment of a method for preparing an antimicrobial and/or antiviral composition suitable for use on a surface comprises combining an essential oil portion and an effective amount of a volatile liquid carrier such that a majority of the composition readily evaporates after dispersal onto the surface. The antimicrobial and/or antiviral composition may also comprise an effective amount of an essential oil portion to enhance the mood of a human.

The compositions can be prepared using conventional procedures known to a person skilled in the art. In a typical method for preparing the antimicrobial and/or antiviral composition, the essential oil portion and the volatile liquid carrier can be prepared independently before being combined together. For example, the essential oil portion can be prepared that comprises at least one essential oil. A volatile liquid carrier can be prepared that comprises at least one alcohol. Optional components, such as water and an antiseptic, may also be added. Then the essential oil portion and the volatile liquid carrier can be combined together to produce the antimicrobial and/or antiviral composition of the present invention. The resulting composition can then be agitated in an agitator as is until the essential oil portion is suitably dispersed in the volatile liquid carrier.

The antimicrobial and/or antiviral compositions can be packaged in any suitable type of container. The composition can be applied to a surface as, for example, a foam, a gel, or a liquid. As a liquid, the composition can be applied, for example, as a spray. Manually operated liquid, foam, or gel dispensing containers known to those skilled in the art may be used. Examples of such containers include, but are not limited to, trigger spray dispensers and pump dispensers. The dispensers can be set to 'mist mode' so as to divide the composition into fine liquid droplets. Typical spray dispensers include atomizers and microsprayers that divide the composition into extremely fine liquid droplets resulting in a fine mist that is directed onto the surface to be treated. In this type of dispenser, the composition is directed through the atomizer or microsprayer dispenser head by energy communicated to a pumping mechanism by the user upon activation of the pumping mechanism. The atomizer or microsprayer dispenser head forces the composition through an obstacle which helps break up the composition to produce the fine liquid droplets resulting in a fine mist. This ensures uniform coverage of the spray onto the surface. Certain containers may be relatively small enough to conveniently fit into a purse, pocket, glove compartment of a car, or onto a hook or holster on a belt. This allows the composition to be portable and available for use at any time as required. For example, the container can be selected to hold approximately 5 ml to 8 ml of the antimicrobial and/or antiviral composition.

The present invention further provides for a method for inhibiting the growth of microorganisms and/or growth and reproduction of viruses, comprising administering to a surface the antimicrobial and/or antiviral composition described herein.

The composition when made in accordance with the present invention can be used on both animate and inanimate surfaces. The composition is non-toxic; that is, it is compatible with and suitable for topical use on human skin. The effective amount of the volatile liquid carrier is such that a majority of the composition readily evaporates after dispersal onto the surface. Consequently, the volatile liquid carrier readily evaporates after dispersal onto the surface. The time for the volatile liquid carrier to evaporate after being dispersed onto the surface will, in part, depend upon the type of dispenser selected for packaging. In one embodiment, both a trigger pump spray dispenser and a pump dispenser set on 'mist mode' will cause the volatile liquid carrier to evaporate within about 15-30 seconds after dispersal onto the surface. In another embodiment, both an atomizer and a microsprayer will cause the volatile liquid carrier to evaporate within about 5-10 seconds after dispersal onto the surface. The essential oil portion remains behind on the surface for a period of time sufficient to enhance the mood of a human in the vicinity of the surface (e.g., at least about 5 minutes, more typically at least about 15 minutes, and most typically at least about 30 minutes). Since the volatile liquid carrier can be so readily evaporable, the composition is ideally suited for application to the surface of any type of electrical device, such as, for example, a computer, a keyboard, a mouse, a stereo, a television set, a portable MP3 player, various kitchen appliances, shavers, and the like.

The other types of hard inanimate surfaces can also include, but are not limited to, surfaces present in kitchens, bathrooms, offices, bedrooms, or car interiors, such as, countertops, tiles, walls, door handles, sinks, dishes, glass, plastic, showers, bath tubs, toilet seats, toys, dashboard, steering wheel, and pet areas. The soft inanimate surfaces can include, but are not limited to, clothing, shoes, upholstered furniture, leather, carpets, and the like.

Other uses of the composition include the addition of the antimicrobial and/or antiviral composition to water, such as water in bath tubs, pools, and hot tubs, to enhance the mood of a human mood.

The antimicrobial and/or antiviral composition described herein can also be used in a medicament for inhibiting growth of microorganisms and/or growth and reproduction of viruses.

It is understood that the term "a" or "an" can also encompass one or more. Any ranges are understood to include the ends of the ranges and any incremental range therein.

The invention will be further understood by the following examples that are not to be construed as a limitation on the invention. Those skilled in the art will appreciate the other and further embodiments are obvious and within the spirit and scope of this invention from the teachings of the present examples taken with the accompanying specification.

EXAMPLES

The following formulations were prepared and tested, and the results are set out below. All volume percentages in these examples are based on the total volume of the antimicrobial and/or antiviral composition. All of the essential oils in these examples are based on those essential oils that are extracted from the stems, flowers and/or fruits of the plants.

Example 1

Formulation 1 consisted of combining about 70% by volume of 95% ethanol, about 5% by volume isopropanol, about 10% by volume water, and about 15% by volume orange oil.

Example 2

Formulation 2 consisted of combining about 65% by volume of 95% ethanol, about 10% by volume lavender oil, about 24% by volume water, and about 1% chlorohexidine gluconate.

Example 3

Formulation 3 consisted of combining about 70% by volume isopropanol and about 10% by volume lemon oil, and about 20% by volume water.

Example 4

Formulation 4 consisted of combining about 62% by volume 95% ethanol, about 7.5% by volume orange oil, about 29.5% by volume water and about 1% by volume chlorohexidine gluconate.

Example 5

Formulation 5 consisted of combining about 72% by volume 95% ethanol, about 12% by volume lavender oil, about 15.5% by volume and about 0.5% by volume chlorohexidine gluconate.

Example 6

Formulation 6 consisted of combining about 70% by volume 95% ethanol, about 10% by volume isopropanol, 10% by volume water and about 10% by volume lemon oil.

Example 7

Formulation 7 consisted of combining about 70% by volume 95% ethanol, about 7.5% by volume orange oil, about 29.5% by volume water and about 1% by volume chlorohexidine gluconate.

Example 8

Formulation 8 consisted of combining about 62% by volume 95% ethanol, about 18% by volume rice bran oil, about 19% by volume water and about 1% by volume chlorohexidine gluconate. This formulation is non-scented.

Example 9

The following Time Kill Test Assay is based on Formulation 7.
Materials

| Test System/Growth Media | | |
|---|---|---|
| Test Organism | ATCC # | Growth Medium |
| *Staphylococcus aureus* | 6538 | Blood Agar |

The microorganism used in this study was obtained from the American Type Culture Collection Manassas, Va.
Recovery Media
Neutralizer: Tryptic Soy Broth with 5% Lecithin and 5% Tween 80 Agar Plate Medium: Blood Agar (BAP)
Methodology
Preparation of Test Substance The test substance was Formulation 7. A 49.0 mL aliquot of the test substance was transferred to a sterile 250 mL flask for use in testing.
Test Organism Preparation Using a stock culture of the test organism, the culture was streaked onto a BAP plate and incubated for 24-48 hours at 35-37° C. On the day of testing, to produce a suspension containing approximately $1 \times 10^8$-$1 \times 10^9$ CFU/mL, a sufficient amount of the 24-48 hour culture from the BAP plate was added to Butterfield's Buffer to yield turbidity equal to 0.5 McFarland Standard.
Test Exposure A 1.0 mL aliquot of the standardized inoculum was added to the test substance representing the start of the test exposure. Immediately, the inoculated test substance was thoroughly mixed by swirling by hand. The inoculated and mixed test substance was held at ambient temperature (20° C.).
Subculture Procedures At 30 second, 1 minute and 2 minute exposure sample times, a 1.0 mL aliquot of the inoculated test substance will be transferred to 49 mL of Tryptic Soy Broth with 5% Lecithin and 5% Tween 80 neutralizer broth ($10^0$ dilution). Two additional 1:10 dilutions in Butterfield's Buffer will be prepared. Using a standard microbiological spread plate count procedure, 1.0 mL aliquots of each dilution ($10^{-1}$-$10^{-2}$) will be plated in duplicate to the appropriate recovery media.

The remaining volume (49 mL) of the neutralized sample ($10^0$ dilution) will be transferred to a sterile 0.2-0.45 µm filter apparatus system pre-wetted with 10 mL sterile diluent. Filter concentrate the sample and rinse the filter using approximately 50 mL sterile diluent. Aseptically remove the filter and place it on the surface of the recovery agar medium.
Reinoculation and Subculture Procedures Immediately prior to reinoculation, a 1.0 mL aliquot of the inoculated test substance will be transferred to 49 mL of Tryptic Soy Broth with 5% Lecithin and 5% Tween 80 neutralizer broth ($10^0$ dilution), serial diluted and plated as stated in the subculture section. The remaining 49 mL aliquot of the neutralized sample ($10^0$) will also be filtered and plated as stated in the subculture section of the protocol. These will be considered the 1 hour, 2 hour and 4 hour exposure time subcultures.

Immediately following this subculture, the test substance will be reinoculated with a 1.0 mL aliquot of the standardized inoculum. At 30 second, 1 minute and 2 minute exposure times after the reinoculation, a 1.0 mL aliquot of the reinoculated test substance will be transferred to 49 mL of Tryptic Soy Broth with 5% Lecithin and 5% Tween 80 neutralizer broth ($10^0$ dilution), serial diluted and plated as stated in the subculture section. The remaining 49 mL aliquot of the neutralized sample ($10^0$) will also be filtered and plated as stated in the subculture section of the protocol. This subculture and reinoculation procedure will be repeated at the Sponsor specified times to evaluate the residual antimicrobial activity of the test substance. After the last reinoculation, the test substance will be evaluated at 30 second, 1 minute, 2 minute and 3 minute exposure times.
Incubation and Observation The bacterial subculture plates were incubated for 48±4 hours at 35-37° C. Following incubation, the agar plates were stored at 2-8° C. for 2 days prior to being observed visually for the presence of growth. The colony forming units were enumerated and the number of survivors at each exposure time was determined. Log and percent reductions were calculated for each time point. Representative subcultures demonstrating growth were appropriately examined for confirmation of the test organism.
Controls
Purity Control A "streak plate for isolation" was performed on the organism culture and following incubation examined in order to confirm the presence of a pure culture. The acceptance criterion for this study control is a pure culture demonstrating colony morphology typical of the test organism.
Neutralizer Sterility Control A representative sample of neutralizer was filtered through a 0.2-0.45 µm filter apparatus system, plated on appropriate recovery media, incubated and observed as in the test. The acceptance criterion for this control is lack of growth.

Test Population Controls

For the initial inoculation, in a similar manner as the culture inoculum was added to the test substance, an equivalent volume of inoculum (1.0 mL) was added to 49.0 mL Butterfield's buffer (same volume as the test substance). This suspension was neutralized as in the test procedure. The suspension was serially diluted and the $10^{-2}$-$10^{-5}$ dilutions were plated using standard microbiological techniques. A new control flask was prepared for each population control determination at each reinoculation. The volume of Butterfield's buffer for the residual test population controls reflected the volume of test substance in the test flask. The first reinoculation contained 46.0 mL of buffer, 43.0 mL for the second reinoculation and 40.0 mL of Butterfield's buffer for the third reinoculation. Following incubation, the organism plates were observed to enumerate the concentration of the test organism present in the test substance at the time of testing (time 0 analysis). The acceptance criterion for this study control is growth and the value is used for calculation purposes only.

Initial Suspension Population Control

The prepared test organism suspension was serially diluted and plated using standard microbiological techniques. Following incubation, the organism plates were observed to enumerate the concentration of the test organism inoculated into the test substance at the time of testing. The acceptance criterion for this study control is growth at $\geq 1.0 \times 10^6$ CFU/mL.

Neutralization Control

To simulate testing conditions, 49 mL of the test substance will be inoculated with 1.0 mL Butterfield's Buffer in place of the test organism suspension (NC Suspension). This control will be performed once and may use multiple dilutions of the test organism.

1. Filtration Neutralization:

Transfer 1.0 mL of the NC Suspension to 49.0 mL neutralizing broth and mix thoroughly. Filter concentrate 49.0 mL of the control suspension and rinse filter as in the test procedure. Add 1.0 mL of an organism suspension containing approximately 100 CFU/mL to the filter apparatus and process through the apparatus. Add 1.0 mL of the organism suspension to a second filter apparatus to be used as an inoculum population control and process. Aseptically transfer the filters to recovery agar plates and incubate. The acceptance criterion for this study control requires the filtration neutralization control and corresponding population control results to be within 1.0 Log.

2. Chemical Neutralization:

Transfer 1.0 mL of the NC Suspension to 49.0 mL neutralizing broth and mix thoroughly. Remove and discard 1.0 mL of the neutralized sample. To the neutralized sample, add 1.0 mL of an organism suspension containing approximately 1000 CFU/mL and mix thoroughly. Plate in duplicate 1.0 mL of neutralized mixture to appropriate recovery medium and incubate. Perform an inoculum population control by adding 1.0 mL of the same organism suspension to 49.0 mL of Butterfield's Buffer and plate in duplicate and incubate. The acceptance criterion for this study control requires the chemical neutralization control and corresponding population control results to be within 1.0 Log.

3a. Due to the increased viscosity of the Tryptic Soy Broth with 5% Lecithin and 5% Tween 80 neutralizer making it difficult to filter, the protocol is amended to allow for the use of multiple filters in collecting the entire volume of neutralizer in all filter subculture procedures. The total survivors at a particular dilution will be determined by adding together the colonies recovered on each of the filters used.

3b. Due to the turbid nature of the Tryptic Soy Broth with 5% Lecithin and 5% Tween 80 neutralizer, the neutralizer sterility control procedure is amended to be as follows:

A representative sample of neutralizer will be filtered through a 0.2-0.45 µm filter apparatus system, plated on appropriate recovery media, incubated and observed as in the test. The acceptance criterion for this control is lack of growth.

Acceptance Criteria

Test Substance Performance Criteria

This study is designed to examine the rate-of-kill of a test substance after inoculation with a test organism. Results will be expressed in percent and log reduction of the test organism. Minimum percent and log reduction values do not exist to specify a "passing" or "failing" test substance.

Control Acceptance Criteria

The study controls must perform according to the criteria detailed in the study controls description section.

Data Analysis

Calculations

Test Data CFU/mL:

$$\frac{(\text{avg.\# colonies found/plate @ dilution used})(\text{dilution factor})}{(\text{volume of neutralized solution})} \cdot (\text{volume plated})$$

Percent Reduction: [1−(test survivors/test population control)]×100

$Log_{10}$ Reduction: $Log_{10}$ (test population control)−$Log_{10}$ (test survivors)

Results

For Control and Neutralization Results, See Tables 1-4

Data measurements/controls including purity, initial suspension, test population, neutralizer sterility and neutralization confirmation performed within acceptance criteria listed in the study controls section of the protocol.

For Test Results, see Tables 5-6

ANALYSIS AND CONCLUSION

Under the conditions of the study, following an initial inoculation, Formulation 7 demonstrated a >99.9999% or >6.76 log reduction of *Staphylococcus aureus* (ATCC 6538) after 30 second, 1 minute, 2 minute and 1 hour contact times at 20° C.

Under the conditions of the study, following a 1 hour reinoculation, Formulation 7 demonstrated a >99.9999% or >6.64 log reduction of *Staphylococcus aureus* (ATCC 6538) after 30 second, 1 minute, 2 minute and 2 hour (1 hour following 1 hour reinoculation) contact times at 20° C.

Under the conditions of the study, following a 2 hour reinoculation, Formulation 7 demonstrated a >99.9999% or >6.69 log reduction of *Staphylococcus aureus* (ATCC 6538) after 30 second, 1 minute, 2 minute and 4 hour (2 hour following 2 hour reinoculation) contact times at 20° C.

Under the conditions of the study, following a 4 hour reinoculation, Formulation 7 demonstrated a >99.9999% or >6.81 log reduction of *Staphylococcus aureus* (ATCC 6538) after 30 second, 1 minute, 2 minute and 3 minute contact times at 20° C.

Under the conditions of this study, Formulation 7, demonstrated substantial residual antimicrobial activity as indicated by complete organism kill following a 1 hour, 2 hour and 4 hour reinoculation procedure.

TABLE 1

CONTROL RESULTS
The following results from controls confirmed study validity:

| Type of Control | Date Performed | Results |
|---|---|---|
| Purity Control | May 19, 2005 | *Staphylococcus aureus* (ATCC 6538) Pure |
| Neutralizer Sterility Control | | No Growth |

TABLE 2

INITIAL SUSPENSION POPULATION CONTROL

| Test Organism | Date Performed | Result |
|---|---|---|
| *Staphylococcus aureus* (ATCC 6538) | May 19, 2005 | $2.6 \times 10^8$ CFU/mL |

CFU = Colony Forming Unit

TABLE 3

TEST POPULATION CONTROL

| Test Organism | Date Performed | Inoculation Time | Result CFU/mL | $Log_{10}$ |
|---|---|---|---|---|
| *Staphylococcus aureus* (ATCC 6538) | May 19, 2005 | Initial | $5.80 \times 10^6$ | 6.76 |
| | | 1 hour | $4.4 \times 10^6$ | 6.64 |
| | | 2 hours | $4.9 \times 10^6$ | 6.69 |
| | | 4 hours | $6.45 \times 10^6$ | 6.81 |

CFU = Colony Forming Unit

TABLE 4

NEUTRALIZATION CONTROLS

Filtration Neutralization Confirmation Control

| Test Substance | Test Organism | Date Performed | Organism Dilution | Total Number of Survivors Recovered With Product | Numbers Control | $\pm 1.0\ log_{10}$ Pass/Fail |
|---|---|---|---|---|---|---|
| Formulation 7 | *Staphylococcus aureus* | May 19, 2005 | $10^{-7}$ | 13 | 22 | 0.23 Pass |

Chemical Neutralization Confirmation Control

| Test Substance | Test Organism | Date Performed | Organism Dilution | With Product | Numbers Control | $\pm 1.0\ log_{10}$ Pass/Fail |
|---|---|---|---|---|---|---|
| Formulation 7 | *Staphylococcus aureus* | May 19, 2005 | $10^{-6}$ | 3, 1 | 7, 13 | 0.7 Pass |

TABLE 5

TEST RESULTS
Test Substance: Formulation 7

| | | Test Organism: *Staphylococcus aureus* TIME EXPOSURE | | | |
|---|---|---|---|---|---|
| DILUTION | Inoculation Time | 30 seconds | 1 minute | 2 minutes | 1 hour |
| $10^{-1}$ | Initial | 0, 0 | 0, 0 | 0, 0 | 0, 0 |
| $10^{-2}$ | | 0, 0 | 0, 0 | 0, 0 | 0, 0 |
| Filtration of 49 mL at $10^0$ dilution | | Filter #1 = 0 Filter #2 = 0 Filter #3 = 0 | Filter #1 = 0 Filter #2 = 0 Filter #3 = 0 | Filter #1 = 0 Filter #2 = 0 Filter #3 = 0 | Filter #1 = 0 Filter #2 = 0 Filter #3 = 0 |

| | | Test Organism: *Staphylococcus aureus* TIME EXPOSURE | | | |
|---|---|---|---|---|---|
| DILUTION | Inoculation Time | 30 seconds | 1 minute | 2 minutes | 2 hours* |
| $10^{-1}$ | 1 hour | 1, 0 | 0, 0 | 0, 0 | 0, 0 |
| $10^{-2}$ | | 0, 0 | 0, 0 | 0, 0 | 0, 0 |

TABLE 5-continued

TEST RESULTS
Test Substance: Formulation 7

| Filtration of 49 mL at $10^0$ dilution | Filter #1 = 0<br>Filter #2 = 0<br>Filter #3 = 0 | Filter #1 = 0<br>Filter #2 = 0<br>Filter #3 = 0 | Filter #1 = 0<br>Filter #2 = 0<br>Filter #3 = 0 | Filter #1 = 0<br>Filter #2 = 0<br>Filter #3 = 0 |
|---|---|---|---|---|

*1 hour following 1 hour reinoculation.

Test Organism: *Staphylococcus aureus*

| | Inoculation | TIME EXPOSURE | | | |
|---|---|---|---|---|---|
| DILUTION | Time | 30 seconds | 1 minute | 2 minutes | 4 hours* |
| $10^{-1}$ | 2 hours | 0, 0 | 0, 0 | 0, 0 | 0, 0 |
| $10^{-2}$ | | 0, 0 | 0, 0 | 0, 0 | 0, 0 |
| Filtration of 49 mL at $10^0$ dilution | | Filter #1 = 0<br>Filter #2 = 0<br>Filter #3 = 0 | Filter #1 = 0<br>Filter #2 = 0<br>Filter #3 = 0 | Filter #1 = 0<br>Filter #2 = 0<br>Filter #3 = 0 | Filter #1 = 0<br>Filter #2 = 0<br>Filter #3 = 0 |

*2 hours following 2 hour reinoculation.

Test Organism: *Staphylococcus aureus*

| | Inoculation | TIME EXPOSURE | | | |
|---|---|---|---|---|---|
| DILUTION | Time | 30 seconds | 1 minute | 2 minutes | 3 minutes |
| $10^{-1}$ | 4 hours | 0, 0 | 0, 0 | 0, 0 | 0, 0 |
| $10^{-2}$ | | 0, 0 | 0, 0 | 0, 0 | 0, 0 |
| Filtration of 49 mL at $10^0$ dilution | | Filter #1 = 0<br>Filter #2 = 0<br>Filter #3 = 0 | Filter #1 = 0<br>Filter #2 = 0<br>Filter #3 = 0 | Filter #1 = 0<br>Filter #2 = 0<br>Filter #3 = 0 | Filter #1 = 0<br>Filter #2 = 0<br>Filter #3 = 0 |

TABLE 6

CALCULATED DATA
Test Substance: Formulation 7

Initial Inoculation Results

| Test Organism | Exposure Time | Test Population Control (CFU/mL) | Number of Survivors (CFU/mL) | Number of Survivors ($Log_{10}$) | Percent Reduction | $Log_{10}$ Reduction |
|---|---|---|---|---|---|---|
| *Staphylococcus aureus* | 30 seconds | $5.80 \times 10^6$ ($Log_{10}$ = 6.76) | <1 | 0 | >99.9999% | >6.76 |
| | 1 minute | | <1 | 0 | >99.9999% | >6.76 |
| | 2 minutes | | <1 | 0 | >99.9999% | >6.76 |
| | 1 hour | | <1 | 0 | >99.9999% | >6.76 |

1 Hour Inoculation Results

| Test Organism | Exposure Time | Test Population Control (CFU/mL) | Number of Survivors (CFU/mL) | Number of Survivors ($Log_{10}$) | Percent Reduction | $Log_{10}$ Reduction |
|---|---|---|---|---|---|---|
| *Staphylococcus aureus* | 30 seconds | $4.4 \times 10^6$ ($Log_{10}$ = 6.64) | <1 | 0 | >99.9999% | >6.64 |
| | 1 minute | | <1 | 0 | >99.9999% | >6.64 |
| | 2 minutes | | <1 | 0 | >99.9999% | >6.64 |
| | 2 hours* | | <1 | 0 | >99.9999% | >6.64 |

*1 hour following 1 hour reinoculation.

2 Hour Inoculation Results

| Test Organism | Exposure Time | Test Population Control (CFU/mL) | Number of Survivors (CFU/mL) | Number of Survivors ($Log_{10}$) | Percent Reduction | $Log_{10}$ Reduction |
|---|---|---|---|---|---|---|
| *Staphylococcus aureus* | 30 seconds | $4.9 \times 10^6$ ($Log_{10}$ = 6.69) | <1 | 0 | >99.9999% | >6.69 |
| | 1 minute | | <1 | 0 | >99.9999% | >6.69 |
| | 2 minutes | | <1 | 0 | >99.9999% | >6.69 |
| | 4 hours* | | <1 | 0 | >99.9999% | >6.69 |

CFU = Colony Forming Units
*2 hours following 2 hour reinoculation.

TABLE 6-continued

CALCULATED DATA
Test Substance: Formulation 7

4 Hour Inoculation Results

| Test Organism | Exposure Time | Test Population Control (CFU/mL) | Number of Survivors (CFU/mL) | Number of Survivors ($Log_{10}$) | Percent Reduction | $Log_{10}$ Reduction |
|---|---|---|---|---|---|---|
| Staphylococcus aureus | 30 seconds | 6.45 × 10$^6$ ($Log_{10}$ = 6.81) | <1 | 0 | >99.9999% | >6.81 |
| | 1 minute | | <1 | 0 | >99.9999% | >6.81 |
| | 2 minutes | | <1 | 0 | >99.9999% | >6.81 |
| | 3 minutes | | <1 | 0 | >99.9999% | >6.81 |

CFU = Colony Forming Units

While the present invention has been described with reference to what are presently considered to be preferred embodiments, it is to be understood that the invention is not limited to these embodiments. To the contrary, the invention is intended to cover various modifications and equivalent arrangements included within the spirit and scope of the appended claims.

The invention claimed is:

1. An antimicrobial and/or antiviral composition for administration to the surface of human skin, the composition comprising:
   an essential oil portion;
   a volatile liquid carrier in an amount that is effective to provide for a majority of the composition to evaporate after dispersal onto the surface;
   water;
   chlorhexidine gluconate present in an amount of about 1% by volume based on the total volume of the composition;
   wherein the amount of the volatile liquid carrier is from about 60% to about 75% by volume based on the total volume of the antimicrobial and/or antiviral composition; and
   wherein the essential oil portion comprises orange oil in an amount between about 5% and 15% by volume based on the total volume of the composition;
   wherein, after administering the composition to the surface of human skin, the composition demonstrates residual antimicrobial activity when maintained at 20° C. such that, four hours after the administration of the composition to the surface of human skin, the composition provides >99.99% reduction of Staphylococcus aureus within three minutes of Staphylococcus aureus inoculation.

2. A composition according to claim 1, wherein the volatile liquid carrier is at least one alcohol containing between 1 to 4 carbon atoms.

3. A composition according to claim 1, wherein the volatile liquid carrier is selected from the group consisting of ethanol, isopropanol and mixtures thereof.

4. A composition according to claim 1, wherein the composition is capable of being applied to the surface of the human skin as a spray.

5. A composition according to claim 1, wherein, after administering the composition to the surface of human skin, the composition acts as a barrier against harmful microorganisms and demonstrates residual antimicrobial activity when maintained at 20° C. such that, two hours after the administration of the composition to the surface of human skin, the composition provides >99.999% reduction of Staphylococcus aureus within two minutes of Staphylococcus aureus inoculation.

6. A composition according to claim 1, wherein, after administering the composition to the surface of human skin, the composition acts as a barrier against harmful microorganisms and demonstrates residual antimicrobial activity when maintained at 20° C. such that, one hour after the administration of the composition to the surface of human skin, the composition provides >99.9999% reduction of Staphylococcus aureus within two minutes of Staphylococcus aureus inoculation.

7. A composition according to claim 4, wherein the spray is configured for application via an atomizer.

8. A composition according to claim 4, wherein the spray is configured for application via a microsprayer.

9. A composition according to claim 4, wherein the spray is configured for application via a manually operated trigger spray dispenser.

10. A composition comprising:
    orange oil in an amount of about 6% to about 12% by volume based on the total volume of the composition;
    a volatile liquid carrier in an amount that is effective to provide for a majority of the composition to evaporate after dispersal onto the surface, wherein the amount of the volatile liquid carrier is from about 60% to about 75% by volume based on the total volume of the composition;
    water; and
    chlorhexidine gluconate present in an amount of about 1% by volume based on the total volume of the composition;
    wherein, after administering the composition to the surface of human skin, the composition demonstrates residual antimicrobial activity when maintained at 20° C. such that, four hours after the administration of the composition to the surface of human skin, the composition provides >99.9999% reduction of Staphylococcus aureus (ATCC 6538) within three minutes of Staphylococcus aureus inoculation.

11. A composition according to claim 10, wherein the volatile liquid carrier is at least one alcohol containing between 1 to 4 carbon atoms.

12. A composition according to claim 10, wherein the volatile liquid carrier is selected from the group consisting of ethanol, isopropanol and mixtures thereof.

13. A composition according to claim 10, wherein the composition is capable of being applied to the surface of the human skin as a spray.

14. A composition according to claim 10, wherein the spray is configured for application via an atomizer.

15. A composition according to claim 10, wherein the spray is configured for application via a microsprayer.

16. A composition according to claim 10, wherein the spray is configured for application via a manually operated trigger spray dispenser.

17. A composition according to claim 10, wherein demonstrating >99.9999% reduction of *Staphylococcus aureus* (ATCC 6538) follows a 15 second exposure time in the presence of 5% fetal bovine serum organic soil load.

18. A composition according to claim 10, comprising orange oil in an amount of about 7.5% by volume based on the total volume of the composition.

19. A composition according to claim 10, wherein, after administering the composition to the surface of human skin, the composition demonstrates residual antimicrobial activity when maintained at 20° C. such that, four hours after the administration of the composition to the surface of human skin, the composition provides >99.9999% reduction of *Staphylococcus aureus* (ATCC 6538) within two minutes of *Staphylococcus aureus* inoculation.

20. A composition according to claim 10, wherein, after administering the composition to the surface of human skin, the composition demonstrates residual antimicrobial activity when maintained at 20° C. such that, four hours after the administration of the composition to the surface of human skin, the composition provides >99.9999% reduction of *Staphylococcus aureus* (ATCC 6538) within one minute of *Staphylococcus aureus* inoculation.

21. A composition according to claim 10, wherein, after administering the composition to the surface of human skin, the composition demonstrates residual antimicrobial activity when maintained at 20° C. such that, four hours after the administration of the composition to the surface of human skin, the composition provides >99.9999% reduction of *Staphylococcus aureus* (ATCC 6538) within 30 seconds of *Staphylococcus aureus* inoculation.

22. A composition according to claim 1, wherein the essential oil portion comprises orange oil in an amount between about 6% and 12% by volume based on the total volume of the composition.

23. A composition according to claim 1, wherein the essential oil portion comprises orange oil in an amount of about 7.5% by volume based on the total volume of the composition.

24. A composition according to claim 1, wherein, after administering the composition to the surface of human skin, the composition acts as a barrier against harmful microorganisms and demonstrates residual antimicrobial activity when maintained at 20° C. such that, four hours after the administration of the composition to the surface of human skin, the composition provides >99.999% reduction of *Staphylococcus aureus* within two minutes of *Staphylococcus aureus* inoculation.

25. A composition according to claim 1, wherein, after administering the composition to the surface of human skin, the composition acts as a barrier against harmful microorganisms and demonstrates residual antimicrobial activity when maintained at 20° C. such that, four hours after the administration of the composition to the surface of human skin, the composition provides >99.999% reduction of *Staphylococcus aureus* within one minute of *Staphylococcus aureus* inoculation.

26. A composition according to claim 1, wherein, after administering the composition to the surface of human skin, the composition acts as a barrier against harmful microorganisms and demonstrates residual antimicrobial activity when maintained at 20° C. such that, four hours after the administration of the composition to the surface of human skin, the composition provides >99.999% reduction of *Staphylococcus aureus* within 30 seconds of *Staphylococcus aureus* inoculation.

* * * * *